US007393998B2

(12) United States Patent
Streatfiled et al.

(10) Patent No.: US 7,393,998 B2
(45) Date of Patent: Jul. 1, 2008

(54) COMMERCIAL PRODUCTION OF INSULIN AND INSULIN-LIKE PROTEINS IN PLANTS

(75) Inventors: Stephen Streatfiled, Bryan, TX (US); John Howard, College Station, TX (US)

(73) Assignee: ProdiGene, Inc., Adel, IA (US)

( * ) Notice: Subject to any disclaimer, the term of this patent is extended or adjusted under 35 U.S.C. 154(b) by 957 days.

(21) Appl. No.: 10/383,285

(22) Filed: Mar. 7, 2003

(65) Prior Publication Data

US 2003/0200566 A1 Oct. 23, 2003

Related U.S. Application Data

(60) Provisional application No. 60/362,874, filed on Mar. 8, 2002.

(51) Int. Cl.

| | |
|---|---|
| ***A01H 5/00*** | (2006.01) |
| ***A01H 5/10*** | (2006.01) |
| ***C12N 15/82*** | (2006.01) |
| ***C12N 5/04*** | (2006.01) |

(52) U.S. Cl. ........................ 800/288; 800/278; 800/287; 800/298; 800/320.1; 435/69.1; 435/412

(58) Field of Classification Search ................. 800/278, 800/288, 298, 300.1, 317.1, 320.1

See application file for complete search history.

(56) References Cited

U.S. PATENT DOCUMENTS

| | | | | |
|---|---|---|---|---|
| 6,096,547 | A | 8/2000 | Goodman et al. | 435/419 |
| 6,642,437 | B1 * | 11/2003 | Lemaux et al. | 800/287 |
| 2005/0039235 | A1 | 2/2005 | Moloney et al. | |

FOREIGN PATENT DOCUMENTS

| | | | |
|---|---|---|---|
| CN | 1295129 | | 5/2001 |
| EP | 0437320 | | 7/1991 |
| WO | WO 9821348 | | 5/1998 |
| WO | WO 99/16890 | * | 4/1999 |
| WO | WO 9954452 | | 10/1999 |

OTHER PUBLICATIONS

Hong, et. al. EP 0437320, Recombinant DNA and its use in producing human insulin, published Jul. 17, 1991.(Applicant's IDS).*

Hooker et al, WO 98/21348, Method of Producing Human Growth Factors from Whole Plants or Plant cell cultures, published May 22, 1998. (Applicant's IDS).*

Molecular Cell Biology, Lodish et al, 3rd edition, 1995, Scientific American Books, New York, p. 97, Figure 3-41.*

Takeshi Arakawa, et al. A plant-based cholera toxin B subunit-insulin fusion protein protects against the development of autoimmune diabetes. Nature Biotechnology vol. 16 Oct 1998.

S,-W. Ma, et al, Transgenic plant expressing autoantigens fed to mice to induce oral immune tolerance. Nature Medicine. vol. 3. No. 7. Jul. 1997.

J. A. Galloway and R. E. Chance. Improving Insulin Therapy: Achievements and Challenges. Horm. Metab. Res. 26 (1994) 591-598.

* cited by examiner

*Primary Examiner*—Medina A Ibrahim

(74) *Attorney, Agent, or Firm*—Patricia A. Sweeney

(57) ABSTRACT

Plants are engineered to express proinsulin or insulin. The plants can be used as a source of the protein for a variety of purposes. Plant tissue can be orally administered to animals to replace the necessity of injection of insulin. Alternatively, the protein can be extracted from plant tissue and delivered to animals. Plant produced proteins can also provide a less expensive and more readily available source of the protein as reagents or in other experimentation involving insulin proteins.

4 Claims, 6 Drawing Sheets

Figure 1

TTCGTGAACCAGCACCTCTGCGGCTCCCACCTCGTGGAGGCCCTCTACCTCGTGTGCGG
CGAGCGCGGCTTCTTCTACACCCCGAAGACCCGCAGGGAGGCCGAGGACCTCCAGGTGG
GCCAGGTGGAGCTCGGCGGTGGCCCGGGCGCCGGCTCCCTCCAGCCGCTCGCCCTCGAG
GGCTCCCTCCAGAAGCGCGGTATCGTGGAGCAGTGCTGCACCTCTATCTGCTCCCTCTA
CCAGCTCGAGAACTACTGCAAC

Figure 2

MANKHLSLSLFLVLLGLSASLASGFVNQHLCGSHLVEALYLVCGERGFFYTPKTRREAE
DLQVGQVELGGGPGAGSLQPLALEGSLQKRGIVEQCCTSICSLYQLENYCN

COMMERCIAL PRODUCTION OF INSULIN AND INSULIN-LIKE PROTEINS IN PLANTS

This application claims priority to previously filed and co-pending application U.S. Ser. No. 60/362,874; this application and all references cited herein are incorporated herein by reference.

BACKGROUND OF THE INVENTION

Over the past decade, transgenic plants have been successfully used to express a variety of proteins in plants, including genes from bacterial and viral pathogens. Numerous genes have been cloned into a variety of transgenic plants including many enzymes that have demonstrated the same enzymatic activity as their authentic counterparts. See, for example, expression of avidin in plants, U.S. Pat. No. 5,767,379; aprotinin expressed in plants, U.S. Pat. No. 5,824,870 and proteases expressed in plants, U.S. Pat. No. 6,087,558.; Hood, E. E., D. R. Withcher, S. Maddock, T. Meyer, C. B. M. Baszczynski, M. Bailey, P. Flynn, J. Register, L. Marshal, D. Bond, E. Kulisek, A. Kusnadi, R. Evangelista, Z. Nikolov, C. Wooge, R. J. Mehigh, R. Hernan, W. K. Kappel, D. Ritland, P. C. Li, and J. A. Howard, 1997, Commercial production of avidin from transgenic maize: characterization of transformant, production, processing, extraction and purification. *Molecular Breeding* 3:291-306; Pen, J., L. Molendijk, W. J. Quax, P. C. Sijmons, A. J. van Ooyen, P. J. van den Elzen, K. Rietveld, and A. Hoekema, 1992, Production of active *Bacillus licheniformis* α-amylase in tobacco and its application in starch liquefaction. *Biotechnology* 10:292-296; Trudel, J., C. Potvin, and A. Asselin 1992 Expression of active hen egg white lysozyme in transgenic tobacco. *Plant Sci.* 87:55-67.

Many additional genes have been expressed in plants solely for their immunogenic potential, including viral proteins (U.S. Pat. No.6,136,320; Mason, H. S., J. M. Ball, J.-J. Shi, X. Jiang, M. K. Estes, and C. J. Arntzen. 1996. Expression of Norwalk virus capsid protein in transgenic tobacco and potato and its oral immunogenicity in mice. *Proc. Natl. Acad. Sci. USA* 93:5335-5340; Wigdorovitz, supra; Kapusta, et al, supra; McGarvey, P. B., J. Hammond, M. M. Dienelt, D. C. Hooper, Z. F. Fu, B. Dietzschold, H. Koprowski, and F. H. Michaels. 1995. Expression of the rabies virus glycoprotein in transgenic tomatoes. *Biotechnology* 13:1484-1487; Thanavala, Y., Y. -F. Yang, P. Lyons, H. S. Mason, and C. J. Arntzen. 1995. Immunogenicity of transgenic plant-derived hepatitis B surface antigen. *Proc. Natl. Acad. Sci. USA* 92:3358-3361) and subunits of bacterial toxins (Arakawa, T., D. K. X. Chong, J. L. Merritt, W. H. R. Langridge. 1997. Expression of cholera toxin B subunit oligomers in transgenic potato plants. *Transgenic Res.* 6:403-413; Arakawa, T., J. Yu, and W. H. Langridge. 1999. Food plant-delivered cholera toxin B subunit for vaccination and immunotolerization. *Adv. Exp. Med. Biol.* 464:161-178; Haq, T. A., H. S. Mason, J. D. Clements, and C. J. Arntzen. 1995. Oral immunization with a recombinant bacterial antigen produced in transgenic plants. *Science* 268:714-716). Animal and human immunization studies have demonstrated the effectiveness of many plant derived recombinant antigens in stimulating the immune system. The production of antigen-specific antibodies and protection against subsequent toxin or pathogen challenge demonstrates the feasibility of plant derived-antigens for immunologic use. For example, the resulting peptides induced an immunogenic response in mice (Mason, H. S., T. A. Haq, J. D. Clements, C. J. Arntzen. 1998. Edible vaccine protects mice against *Escherichia coli* heat-labile enterotoxin (LT): potatoes expressing a synthetic LT-B gene. Vaccine 16:1336-1343; Wigdorovitz, A., C. Carrillo, M. J. Dus Santos, K. Trono, A. Peralta, M. C. Gomez, R. D. Rios, P. M. Franzone, A. M. Sadir, J. M. Escribano, M. V. Borca. 1999. Induction of a protective antibody response to foot and mouth disease virus in mice following oral or parenteral immunization with alfalfa transgenic plants expressing the viral structural protein VP1. *Virology* 255:347-353), and humans (Kapusta, J., M. Modelska, M. Figlerowicz, T. Pniewski, M. Letellier, O. Lisowa, V. Yusibov, H. Koprowski, A. Plucienniczak, A. B. Legocki. 1999. A plant-derived edible vaccine against hepatitis B virus. *FASEB J.* 13:1796-1799) comparable to that of the original pathogen. Characterization studies of these engineered immunogens have proven the ability of plants to express, fold and modify proteins in a manner that is consistent with the native source.

The utilization of transgenic plants for vaccine production has several potential benefits over traditional vaccines. First, transgenic plants are usually constructed to express only a small antigenic portion of the pathogen or toxin, eliminating the possibility of infection or innate toxicity of the whole organism and reducing the potential for adverse reactions. Second, since there are no known human or animal pathogens that are able to infect plants, concerns with viral or prion contamination are eliminated. Third, immunogen production in transgenic crops relies on the same established technologies to sow, harvest, store, transport, and process the plant as those commonly used for food crops, making transgenic plants a very economical means of large-scale vaccine production. Fourth, expression of immunogens in the natural protein-storage compartments of plants maximizes stability, minimizes the need for refrigeration and keeps transportation and storage costs low (Lamphear, B. J., S. J. Streatfield, J. M. Jilka, C. A. Brooks, D. K. Barker, D. D. Turner, D. E. Delaney, M. Garcia, B. Wiggins, S. L. Woodard, E. E. Hood, I. R. Tizard, B. Lawhorn, J. A. Howard. 2002. Delivery of subunit vaccines in maize seed. *J. Control. Release* 85:169-180). Fifth, formulation of multicomponent vaccines is possible by blending the seed of multiple transgenic corn lines into a single vaccine. Sixth, direct oral administration is possible when immunogens are expressed in commonly consumed food plants, such as grain, leading to the production of edible vaccines.

Some of the first edible vaccine technologies developed include transgenic potatoes expressing the *E. coli* heat-labile enterotoxin (LT-B) or a Hepatitis B surface antigen (HbsAg); (Thanavala, supra; Arntzen, C. J., D. M. -K. Lam. 2000. Vaccines expressed in plants. U.S. Pat. No. 6,136,320; Lam, D. M. -K., C. J. Arntzen, H. S. Mason. 2000. Vaccines expressed in plants. U.S. Pat. No. 6,034,298; Arntzen, C. J., D. M. -K. Lam. 1999. Vaccines expressed in plants. U.S. Pat. 5,914,123; Lam, D. M. -K., C. J. Arntzen. 1997. Anti-viral vaccines expressed in plants. U.S. Pat. No. 5,612,487; Lam, D. M., C. J. Arntzen. 1996. Vaccines produced and administered through edible plants. U.S. Pat. No. 5,484,719), and a Norwalk virus surface protein (Mason, 1996, supra). In addition to human viral targets, two proteins specific for livestock viruses have also been expressed in plants and fed to animals to test for immune responses, VP1 protein for foot-and-mouth disease (Wigdorovitz, supra; Carillo, C., A. Wigdorovitz, J. C. Oliveros, P. I. Zamorano, A. M. Sadir, N. Gomez, J. Salinas, J. M. Escribano, M. V. Borca. 1998. Protective immune response to foot-and-mouth disease virus with VP1 expressed in transgenic plants. *J. Virology* 72:1688-1690) and Transmissable Gasteroenteritis Virus (Jilka, J. Immunogenicity of TGEV spike protein expressed in transgenic maize seed: preliminary swine trials. PCT/US01/01148)

One of the most promising aspects of edible vaccines is the ability of orally administered immunogens to stimulate a mucosal immune response (Ruedl, C. and H. Wolf. 1995. Features of oral immunization. *Int. Arch. Allergy Immunol.* 108:334-339). Mucosal surfaces, the linings of the respiratory, gastrointestinal, and urogenital tracts, play an important physical and chemical role in protecting the body from invading pathogens and harmful molecules. The mucosal immune system is distinct and independent of the systemic, or humoral, immune system, and is not effectively stimulated by parenteral administration of immunogens (Czerkinsky, C., A. M. Svennerholm, and J. Holmgren. 1993. Induction and assessment of immunity at enteromucosal surfaces in humans: implications for vaccine development. *Clin. Infect. Dis.* 16 Suppl 2:S106-S116). Rather, the mucosal immune system requires antigen presentation directly upon the mucosal surfaces (Jilka, J. Immunogenicity of TGEV spike protein expressed in transgenic maize seed: preliminary swine trials. WO 01/51080; Bailey, M. R. 2000. A model system for edible vaccination using recombinant avidin produced in corn seed. M. S. degree thesis, Texas A&M University). Since most invading pathogens first encounter one or more of the mucosal surfaces, stimulation of the mucosal immune system is often the best first defense against many transmissible diseases entering the body through oral, respiratory and urogenital routes (Holmgren, J., C. Czerkinsky, N. Lycke, and A. M. Svennerholm. 1994. Strategies for the induction of immune responses at mucosal surfaces making use of cholera toxin B subunit as immunogen, carrier, and adjuvant. *Am. J Trop. Med. Hyg.* 50:42-54).

Diabetes mellitus is a serious and chronic disorder that affects 6% of the world's population and all ethnic groups. In the United States, approximately 5% of the population has diabetes. Symptoms of diabetes include hyperglycemia and reduced production or release of insulin or response to insulin. Diabetes mellitus is classified into two types, type I diabetes or insulin-dependent diabetes mellitus (IDDM) and type II diabetes or non-insulin-dependent diabetes mellitus (NIDDM). Type I diabetes, in which the pancreas has stopped producing insulin, affects 10% of all diabetics, often begins in childhood and is known as juvenile onset diabetes. Significant recent research has focused on the development of molecules for treatment of insulin-dependant diabetes mellitus. This autoimmune disease results in the destruction of insulin-producing pancreatic cells. Eisenbarth, G. (1985) *N. Eng. J. Med* 314:1360-1388. In the more prevalent type II diabetes, affecting 90% of all diabetics, the pancreas can produce insulin, but insulin secretion in response to meals is diminished, and the diabetic's tissues, are not as responsive to insulin as tissues from a non-diabetic. Type II diabetes is also known as adult onset diabetes.

Diminished response to or low levels of insulin result in chronic high levels of blood glucose, which gradually alters normal body chemistry and leads to failure of the microvascular system in many organs. This leads to dire consequences. For example, in the United States, diabetes is the largest cause of blindness, is involved in about 70% of amputations, and is the cause of kidney failure in 33% of patients requiring dialysis. Medical treatment of side effects of diabetes and lost productivity due to inadequate treatment of diabetes are estimated to have an annual cost of about $40 billion in the United States alone.

It has long been a goal of insulin therapy to mimic the pattern of endogenous insulin secretion in normal individuals. The daily physiological demand for insulin fluctuates and can be separated into two phases: (a) the absorptive phase requiring a pulse of insulin to dispose of the meal-related blood glucose surge, and (b) the post-absorptive phase requiring a sustained delivery of insulin to regulate hepatic glucose output for maintaining optimal fasting blood glucose. Accordingly, effective therapy for people with diabetes generally involves the combined use of two types of exogenous insulin formulations: a fast-acting meal time insulin provided by bolus injections and a long-acting, so-called, basal insulin, administered by injection once or twice daily to control blood glucose levels between meals.

The nine-year Diabetes Control and Complications Trial (DCCT), which involved 1441 type I diabetic patients, demonstrated that maintaining blood glucose levels within close tolerances reduces the frequency and severity of diabetes complications. Conventional insulin therapy involves only two injections per day. The intensive insulin therapy in the DCCT study involved three or more injections of insulin each day. In this study the incidence of diabetes-side effects was dramatically reduced. For example, retinopathy was reduced by 50-76%, nephropathy by 35-56%, and neuropathy by 60% in patients employing intensive therapy.

Unfortunately, many diabetics are unwilling to undertake intensive therapy due to the discomfort associated with the many injections required to maintain close control of glucose levels. A non-injectable form of insulin is desirable for increasing patient compliance with intensive insulin therapy and lowering their risk of complications. Many investigators have studied alternate routes for administering insulin, such as oral, rectal, transdermal, and nasal routes. So far, these types of administration have not been effective due to poor insulin absorption, low serum insulin concentration, irritation at the site of delivery, or lack of significant decrease in serum glucose levels. Therefore, there remains a need for an effective system for administration of a long-acting insulin.

The source of most insulin today is isolation from human, bovine or pork tissue or serum, or from recombinant microorganisms; yeast or the bacteria *E. coli*. Demand for the compound is huge. When attempts have been made to provide non-injection routes of insulin administration, the amount required increases further. Currently, insulin is a three billion to five billion dollar market. Several metric tons are provided yearly. With non-injection methods, volume is predicted to increase ten times. Clearly, any reduction in cost would be advantageous, along with the ability to produce large quantities in an easily transported and stored manner. Still further, an oral delivery method would provide a highly desirable alternative to current choices of administering insulin.

With adequate expression levels, large quantities of proinsulin or insulin could be produced, very economically, for pharmeceutical and other uses. Insulin is also useful, in addition to its role in treatment of diabetics, for research and related purposes. For example, in addition to its role in vivo, insulin is also useful in recombinant cell culture. Insulin is an example of a polypeptide factor important for mammalian cell culture proliferation and anabolism. Some cell cultures produce endogenous insulin and some do not; cell cultures which rely on added insulin are problematic because insulin is unstable in some cultures. European publication number, 0307247A2, published Mar. 3, 1989, describes the introduction of nucleic acid encoding insulin into a mammalian host cell to eliminate the need for adding exogenous insulin.

Production of insulin in plants would overcome problems associated with current production methods, such as the limited amount of insulin and proinsulin which is available from animal and bacteria and yeast sources, and purity issues. Attempts have been made to express insulin and another protein associated with diabetes, glutamate decarboxylase, in plants. Indeed, initial attempts did not use the insulin or proinsulin gene, but rather the diabetes-associated autoantigen, glutamic acid decarboxylase was expressed in potato and tobacco. Ma et al., *Nature Medicine* (1997) 3(7):793-796. Also, potato plants were transformed with the proinsulin gene fused to cholera toxin B subunit as discussed in Arakawa et al. *Nature Biotechnology* (1998) 16:934-938. This resulted in the fusion protein being produced at up to 0.05% of total soluble protein. However, fusion of insulin with the cholera toxin B subunit may not always be desirable. These experiments were conducted with dicotyledonous plants. The inventors have discovered it is not necessary to fuse insulin with cholera toxin B subunit in order to achieve expression.

SUMMARY OF THE INVENTION

The invention is the expression of an insulin compound in plants. In a preferred embodiment, the proinsulin and/or insulin proteins are expressed in monocotyledonous plants. In a further preferred embodiment, they are expressed in maize. The proteins may be extracted from the plant, or the plant tissue used in various applications. In one such application, the plant tissue can be orally administered to an animal. In yet another embodiment, a biomass is created by expressing the proteins in a plurality of plants where at least some of the plants express the proteins, then harvesting the biomass.

BRIEF DESCRIPTION OF THE DRAWINGS

FIG. 1 is the human proinsulin-encoding nucleotide sequence. (SEQ ID NO:1).

FIG. 2 is the amino acid sequence of the barley alpha amylase signal sequence (underlined) fused to human proinsulin. (SEQ ID NO: 2).

DESCRIPTION

Figure 3:
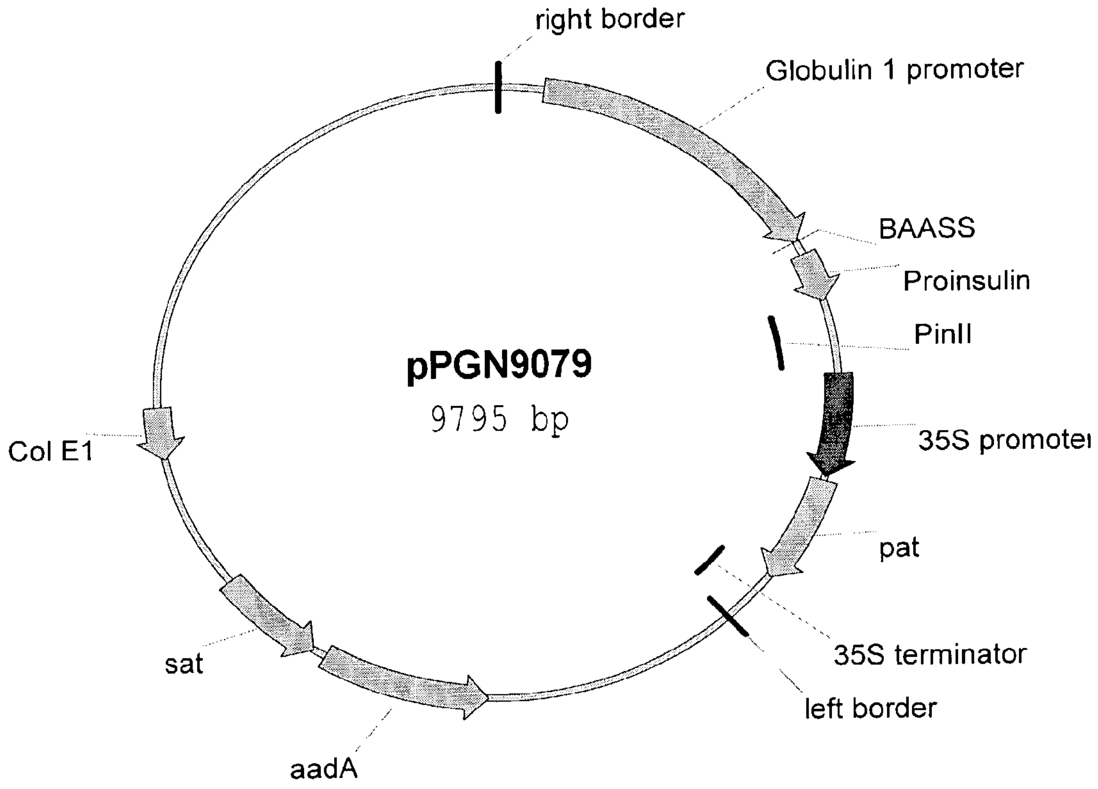
FIG. 3 is the vector used to transform plants with the proinsulin-encoding nucleotide sequence.

This invention relates to the expression of proinsulin and insulin in plants, where the plants express at high levels. This invention further relates to stable transformation of plants with such proteins. As used herein stable transformation refers to the transfer of a nucleic acid fragment into a genome of a host organism resulting in genetically stable inheritance.

The term "insulin" as used herein refers to mammalian insulin, such as bovine, porcine or human insulin, whose sequences and structures are known in the art. Bovine, porcine, and human insulin are preferred mammalian insulins; human insulin is more preferred. The amino acid sequence and spatial structure of human insulin are well-known. Human insulin is comprised of a twenty-one amino acid A-chain and a thirty amino acid B-chain which are cross-linked by disulfide bonds. A properly cross-linked human insulin contains three disulfide bridges: one between position 7 of the A-chain and position 7 of the B-chain, a second between position 20 of the A-chain and position 19 of the B-chain, and a third between positions 6 and 11 of the A-chain. The proinsulin molecule also contains a C-chain, which is cleaved by enzymes in the human body. Proinsulin is a single polypeptide chain containing a sequence of about thirty residues that is absent from mature insulin. Proinsulin has a B-C-A chain structure. The C or connecting peptide joins the carboxyl end of the B chain and the amino terminus of the A chain of the future insulin molecule. Biochemistry 3rd edition, pg. 995 (1988) New York, W H Freeman & Co. The mature insulin is generated by cleavage of the C peptide at dibasic residues after Arg(31)-Arg(32) and after Lys(64)-Arg(65). Two distinct processing enzymes have been defined which are specific for their respective dibasic cleavage sites in proinsulin; type I is substrate specific for the BC junction, while type II is specific for the CA junction (Weiss, Biochemistry 29, 1990). When proinsulin is used for manufacture of insulin, enzymes such as trypsin are used to cleave the C-chain and an enzyme such as carboxypeptidase B is used to further remove basic amino acids.

Use of insulin analogs is also included within the scope of the invention and refers to proteins that have an A-chain and a B-chain that have substantially the same amino acid sequences as the A-chain and B-chain of human insulin, respectively, but differ from the A-chain and B-chain of human insulin by having one or more amino acid deletions, one or more amino acid replacements, and/or one or more amino acid additions that do not destroy the insulin activity of the insulin analog. Also included in this invention are analogs of proinsulin, where the C peptide is reduced in length and/or modified in sequence.

Genes which encode insulin and insulin-like proteins are available to one skilled in the art. See for example Galloway, J. A. and Chance, R. E., *Horm. Metab. Res.* (1994) 26:591-598 and Genbank Access no. XP_006400; Arakawa et al., supra; Bell, G. I. et al., (1980) Nature 284:26-32 (human insulin gene). Any gene which encodes proinsulin, insulin or insulin analogs may be used in this invention. Codon optomization for the plant in which the gene is to be inserted can be useful in obtaining high expression levels, as can be removing sequences that may destabilize the mRNA.

The methods available for putting together a gene as described above for the improved expression described above can differ in detail. However, the methods generally include the designing and synthesis of overlapping, complementary synthetic oligonucleotides, which are annealed and ligated together to yield a gene with convenient restriction sites for cloning. PCR-based approaches may be used to attach and link stretches of sequence. Also, subsequent PCR amplification of the product may be necessary before later sub-cloning steps.

Once the gene has been made or isolated which encodes the protein, it is placed into an expression vector by standard methods. The selection of an appropriate expression vector will depend upon the method of introducing the expression vector into host cells. A typical expression vector contains prokaryotic DNA elements coding for a bacterial replication origin and an antibiotic resistance gene to provide for the growth and selection of the expression vector in the bacterial host; a cloning site for insertion of an exogenous DNA sequence, which in this context would code for the protein of interest; eukaryotic DNA elements that control initiation of transcription of the exogenous gene, such as a promoter; and DNA elements that control the processing of transcripts, such as leader and transcription termination/polyadenylation sequences. It also can contain such sequences as are needed for the eventual integration of the vector into the plant chromosome.

In a preferred embodiment, the expression vector also contains a gene encoding a selection marker, which is functionally linked to a promoter and terminator that control transcriptional initiation and termination, respectively. For a general description of plant expression vectors and reporter genes, see Gruber et al. (1993) (Gruber et al., "Vectors for Plant Transformation" in Methods of Plant Molecular Biology and Biotechnology 89-119, CRC Press, 1993).

Promoter elements employed to control expression of the enzyme encoding gene and the selection gene, respectively, can be any plant-compatible promoters. Those can be plant gene promoters, such as, for example, a polyubiquitin promoter, a promoter for the small subunit of ribulose-1,5-bis-phosphate carboxylase, or promoters from the tumor-inducing plasmids from *Agrobacterium tumefaciens*, such as the nopaline synthase and octopine synthase promoters, or viral promoters such as the cauliflower mosaic virus (CaMV) 19S and 35S promoters or the figwort mosaic virus 35S promoter. See Kay et al. (1987) *Science* 236:1299 and European patent application No. 0 342 926. See international application WO 91/19806 for a review of illustrative plant promoters. The range of available plant compatible promoters includes tissue specific and inducible promoters. In one embodiment of the present invention, the exogenous DNA is under the transcriptional control of a plant polyubiquitin promoter. Plant polyubiquitin promoters are well known in the art, as evidenced by European patent application no. 0 342 926.

Alternatively, a tissue specific promoter can be provided to direct transcription of the DNA preferentially to the seed. One such promoter is the globulin promoter. This is the promoter of the maize globulin-1 gene, described by Belanger, F. C. and Kriz, A. L. (1991) *Genetics* 129:863-872. It also can be found as accession number L22344 in the Genebank database. Another example is the phaseolin promoter. See, Bustos et al. (1989) *The Plant Cell Vol.* 1, 839-853.

One option for use of a selectable marker gene is a glufosinate-resistance encoding DNA and in an embodiment can be the phosphinothricin acetyl transferase ("PAT") or maize optimized PAT gene (Jayne et al., U.S. Pat. No. 6,096,947) under the control of the CaMV 35S promoter and terminator. The gene confers resistance to bialaphos. See, Gordon-Kamm et al. (1990) *Plant Cell* 2, 603-618; Uchimiya et al., (1993) *Bio/Technology* 11:835, and Anzai et al., (1989) *Mol. Gen. Genet.* 219:492.

It may also be desirable to provide for inclusion of sequences to direct expression of the protein to a particular part of the cell. A variety of such sequences are known to those skilled in the art. For example, if it is preferred that expression be directed to the cell wall, this may be accomplished by use of a signal sequence and one such sequence is the barley alpha amylase signal sequence, (Rogers, (1985) *J. Biol Chem* 260, 3731-3738). Another example is the brazil nut protein signal sequence when used in canola or other dicotyledons. Another alternative is to express the protein in the endoplasmic reticulum of the plant cell. This may be accomplished by use of a localization sequence, such as KDEL. This sequence contains the binding site for a receptor in the endoplasmic reticulum. Muntro, S. and Pelham, H. R. B. (1987) *Cell* 48:899-907.

Obviously, many variations on the promoters, selectable markers and other components of the construct are available to one skilled in the art.

In accordance with the present invention, a transgenic plant is produced that contains a DNA molecule, comprised of elements as described above, integrated into its genome so that the plant expresses a heterologous protein-encoding DNA sequence. In order to create such a transgenic plant, the expression vectors containing the gene can be introduced into protoplasts, into intact tissues, such as immature embryos and meristems, into callus cultures, or into isolated cells. Preferably, expression vectors are introduced into intact tissues. General methods of culturing plant tissues are provided, for example, by Miki et al., (1993) "Procedures for Introducing Foreign DNA into Plants" in Methods in Plant Molecular Biology and Biotechnology, Glick et al. (eds) pp. 67-68 (CRC Press 1993) and by Phillips et al., (1988) "Cell/Tissue Culture and In Vitro Manipulation" in Corn and Corn Improvement 3d Edit. Sprague et al. (eds) pp. 345-387 (American Soc. Of Agronomy 1988). The selectable marker incorporated in the DNA molecule allows for selection of transformants.

Methods for introducing expression vectors into plant tissue available to one skilled in the art are varied and will depend on the plant selected. Procedures for transforming a wide variety of plant species are well known and described throughout the literature. See, for example, Miki et al., supra; Klein et al., (1992) *Bio/Technology* 10:286-291; and Weisinger et al., (1988) *Ann. Rev. Genet.* 22: 421-477. For example, the DNA construct may be introduced into the genomic DNA of the plant cell using techniques such as microprojectile-mediated delivery, Klein et al., (1992) supra; electroporation, Fromm et al., (1985) *Proc. Natl. Acad. Sci. USA* 82: 5824-5828; polyethylene glycol (PEG) precipitation, Paszkowski et al., (1984) *EMBO J.* 3: 2717-2722; direct gene transfer, WO 85/01856 and EP No. 0 275 069; in vitro protoplast transformation, U.S. Pat. No. 4,684,611; and microinjection of plant cell protoplasts or embryogenic callus, Crossway, (1985) *Mol. Gen. Genet.* 202:179-185. Cocultivation of plant tissue with *Agrobacterium tumefaciens* is another option, where the DNA constructs are placed into a binary vector system, Ishida et al., (1996) *Nature Biotechnology* 14, 745-750. The virulence functions of the *Agrobacterium tumefaciens* host will direct the insertion of the construct into the plant cell DNA when the cell is infected by the bacteria. See, for example Horsch et al., (1984) *Science* 233: 496-498, and Fraley et al. (1983) *Proc. Natl. Acad. Sci. USA* 80: 4803-4807.

Standard methods for transformation of canola are described by Moloney et al., (1989) *Plant Cell Reports* 8:238-242. Corn transformation is described by Fromm et al., (1990) *Bio/Technology* 8:833-839, and Gordon-Kamm et al., *The Plant Cell* 2:603-618. *Agrobacterium* is primarily used in dicots, but certain monocots such as maize can be transformed by *Agrobacterium*, U.S. Pat. No. 5,550,318. Rice transformation is described by Hiei et al., (1994) *The Plant Journal* 6(2), 271-282, Christou et al., (1991) *Trends in Biotechnology* 10:239. Wheat can be transformed by techniques similar to those used for transforming corn or rice. Sorghum transformation is described by Wan et al., (1994) *Plant Physiol.* 104:37. Soybean transformation is described in a number of publications, including U.S. Pat. No. 5,015,580.

In one preferred method, the *Agrobacterium* transformation methods of Ishida supra and also described in U.S. Pat. No. 5,591,616, are generally followed, with modifications that allow the inventors to recover transformants from HiII maize. The Ishida method uses the A188 variety of maize that produces Type I callus in culture. In one preferred embodiment the High II maize line is used which initiates Type II embryogenic callus in culture. While Ishida recommends selection on phosphinothricin when using the bar or PAT gene for selection, another preferred embodiment provides for use of bialaphos instead.

The bacterial strain used in the Ishida protocol is LBA4404 with the 40 kb super binary plasmid containing three vir loci from the hypervirulent A281 strain. This strain is resistant to tetracycline. The cloning vector cointegrates with the super binary plasmid. Since the cloning vector has an *E. coli* specific replication origin but not an *Agrobacterium* specfiic replication origin, it cannot survive in Agrobacterium without cointegrating with the super binary plasmid. Since the LBA4404 strain is not highly virulent, and has limited application without the super binary plasmid, the inventors have found in yet another embodiment that the EHA101 strain is preferred. It is a disarmed helper strain derived from the hypervirulent A281 strain. The cointegrated super binary/cloning vector from the LBA4404 parent is isolated and electroporated into EHA 101, selecting for spectinomycin resistance. The plasmid is isolated to assure that the EHA101 strain contains the plasmid.

Further, the Ishida protocol as described provides for growing fresh culture of the *Agrobacterium* on plates, scraping the bacteria from the plates, and resuspending in the co-culture medium as stated in the '616 patent for incubation with the maize embryos. This medium includes 4.3 $gl^{-1}$ MS salts, 0.5 $mgl^{-1}$ nicotinic acid, 0.5 $mgl^{-1}$ pyridoxine hydrochloride, 1.0 $mgl^{-1}$ thiamine hydrochloride, 1.0 $gl^{-1}$ casamino acids, 1.5 $mgl^{-1}$ 2,4-Dichlorophenoxyacetic Acid (2,4-D), 68.5 $gl^{-1}$ sucrose and 36 $gl^{-1}$ glucose, all at a pH of 5.8. In a further preferred method, the bacteria are grown overnight in a 1 ml culture, then a fresh 10 ml culture is re-inoculated the next day when transformation is to occur. The bacteria grow into log phase, and are harvested at a density of no more than OD600=0.6 and preferably between 0.2 and 0.5. The bacteria are then centrifuged to remove the media and resuspended in the co-culture medium. Since Hi II is used, medium preferred for Hi II is used. This medium is described in considerable detail by Armstrong, C. I. and Green C. E. "Establishment and maintenance of friable, embryogenic maize callus and involvement of L-proline" *Planta* (1985) 154:207-214. The resuspension medium is the same as that described above. All further Hi II media are as described in Armstrong supra. The result is redifferentiation of the plant cells and regeneration into a plant. Redifferentiation is sometimes referred to as dedifferentiation, but the former term more accurately describes the process where the cell begins with a form and identity, is placed on a medium in which it loses that identity, and becomes "reprogrammed" to have a new identity. Thus the scutellum cells become embryogenic callus.

The levels of expression of the gene of interest can be enhanced by the stable maintenance of a protein encoding gene on a chromosome of the transgenic plant. Use of linked genes, with herbicide resistance in physical proximity to the proinsulin or insulin encoding gene, would allow for maintaining selective pressure on the transgenic plant population and for those plants where the genes of interest are not lost.

With transgenic plants according to the present invention, protein can be produced in commercial quantities. Thus, the selection and propagation techniques described above yield a plurality of transgenic plants, which are harvested in a conventional manner. The plant with the protein can be used in the processing, or the protein extracted. Protein extraction from biomass can be accomplished by known methods which are discussed, for example, by Heney and Orr, (1981) *Anal. Biochem.* 114: 92-96.

It is evident to one skilled in the art that there can be loss of material in any extraction method used. Thus, a minimum level of expression is required for the process to be economically feasible. For the relatively small number of transgenic plants that show higher levels of expression, a genetic map can be generated, via conventional RFLP and PCR analysis, which identifies the approximate chromosomal location of the integrated DNA molecule. For exemplary methodologies in this regard, see Glick and Thompson (1993), in Methods in Plant Molecular Biology and Biotechnology, 269-84 (CRC Press 1993).

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

In one embodiment of the invention, a biomass is created by producing a plurality of plants by the methods described above, where at least some of the plants express the proinsulin or insulin proteins. The biomass created is then harvested. The plants may be used as the source of the proteins, with all or part of the plant used as the protein source. In a preferred embodiment of the invention, seed is used as the source of the proteins. This is particularly preferred when a promoter preferentially expressing the proteins in the seed is used. Alternatively, the protein may be extracted by wet milling, dry milling or any one of numerous procedures available.

EXAMPLE 1

Introduction of DNA into Plants

Introduction of a nucleotide sequence encoding proinsulin protein in maize seed was achieved as follows.

The proinsulin-encoding nucleotide sequence used in this example is set forth in FIG. 1 (SEQ ID NO: 1), having been synthesized for codon optimization in maize, and ensuring no sequences were present that are predicted may destabilize the mRNA.

The protein encoded by the sequence is set forth in FIG. 2 along with 24 extra N-terminal amino acids encoding the barley alpha amylase signal sequence (SEQ ID NO: 2). Thus, the proinsulin protein consists of the 86 C-terminal amino acids of the 110 amino acids given in FIG. 2. Once the signal sequence is lost and proinsulin cleaved, 51 amino acids comprising insulin will remain the human form of proinsulin is given.

Immature embryos of corn (*Zea mays* L.) were isolated from greenhouse-grown ears at 9-13 days after pollination depending on embryo size, generally 1.5-2.0 mm long. The embryos were treated with *A. tumefaciens* containing the DNA construct PGN9079 which carries the proinsulin gene under the control of maize globulin1 promoter sequence (PGN9066; Belanger & Kriz, supra). The construct also contained a barley α-amylase signal sequence (BAASS; Rogers et al. 1985 *J. Biol. Chem.* 260, 3731-3738), for targeting the protein into the cell wall, and the plant transcription unit (PTU) was terminated by the pinII terminator, (An et al., 1989, *Plant Cell* 1: 115-122. The PTU was positioned 5' of a CAMV 35S-pat-35S PTU encoding resistance to the selective agent bialaphos. See FIG. 3.

The treated embryos were plated onto callus induction medium and incubated in the dark at 19° C. for four days. The embryos were then transferred to callus maintenance medium (CMM) and cultured in the dark at 28° C. They were transferred every two weeks to fresh CMM medium. The callused embryos ceased growing after about two weeks on bialaphos and eventually turned brown. Transgenic calli appeared as early as six weeks following treatment but the majority of transformation events appeared at seven to nine weeks after treatment. The transgenic calli were easily spotted due to their white to pale yellow color, Type II callus phenotype, and rapid growth rate.

The transgenic events were grown for approximately four more weeks on bialaphos selection and then plated onto regeneration medium in the dark at 28° C. for somatic embryo production. The somatic embryos were removed after three weeks and plated onto germination medium in the light (20-30 $\mu molessec^{-1}m^{-2}$) at 25 embryos per plate at 28° C. The embryos germinated after 7-21 days and the $T_0$ plantlets were moved into 25 mm×150 mm tubes containing 40 ml of minimal medium and left in the light as above for at least one week for further shoot and root development.

The plants were transferred into flats filled with equal parts of SunGro High Porosity (SunGro Horticulture Inc.) and Metro Mix 700 (Scott's-Sierra Horticultural Products Co.), covered with humidomes and placed in growth chambers for three to four weeks at 28° C. and 90 μmolessec$^{-1}$m$^{-2}$. Humidomes were removed after one week. Plants were transplanted into 2 gal pots filled with High Porosity potting media and 27 g of Sierra 17-6-12 slow release fertilizer mixed into the top media surface. Plants were moved to the greenhouse floor (27° C. and 195 μmolessec$^{-1}$m$^{-2}$). The $T_0$ plants were pollinated with pollen from greenhouse-grown maize plants of elite germplasm.

EXAMPLE 2

Expression in Plant Tissues

Callus tissue was homogenized or individual seeds were pulverized and homogenized with PBST (phosphate-buffered saline with 0.05% Tween-20™). Cell debris was removed by centrifugation. Total protein concentration was determined by the microtiter method (Bio-Rad, Richmond, Calif.) according to the method of Bradford (Bradford, M. M. 1976. A rapid and sensitive method for the quantitation of microgram quantities of protein utilizing the principal of protein-dye binding. Anal. Biochem. 72:248-254).

ELISA assays were performed as follows. Insulin standard was obtained from Roche (Cat. No. 1376497) and a portion was then biotinylated using a biotinylation kit (Roche, Cat. No. 1418165). Nunc MaxiSorp microtiter plates were coated by using insulin coating antibody (E6E5) 1.0 mgml$^{-1}$ in PBS containing 0.1% sodium azide and diluting it 1:2000 in coating buffer. 100 μl was added per well and the pates covered and placed at 4° C. on a flat surface for 12-24 hours. The next day, plates were washed four times with PBST. 200 μl blocking solution (3% BSA in PBST) was added to each well. The plates were covered and incubated at 35° C. to 39° C. with a target temperature of 37° C. for 50-70 minutes, with a target time of one hour. The plate was then washed four times with PBST.Biotinylated insulin was diluted 1:90,000 in competition buffer (1% BSA in PBST) in two dilutions (first 1:90 by diluting 3 μl biotinylated insulin stock into 267 μl buffer, and then 1:1000 as 10 μl into 10 ml competition buffer). 90 μl of solution was added to each well on the plate.

An insulin standard was created, and the stock serially diluted as shown:

| | |
|---|---|
| 32 ng/10 μl | 4 μl Insulin + 1.246 ml PBST |
| 16 ng/10 μl | 300 μl of A + 300 μl PBST |
| 8 ng/10 μl | 300 μl of B + 300 μl PBST |
| 4 ng/10 μl | 300 μl of C + 300 μl PBST |
| 2 ng/10 μl | 300 μl of D + 300 μl PBST |
| 1 ng/10 μl | 300 μl of E + 300 μl PBST |
| 0.5 ng/10 μl | 300 μl of F + 300 μl PBST |

10 μl of each standard was loaded into the appropriate wells to yield a standard curve from 0.5 to 32 ng. Up to 1 μg of the unknown protein sample was loaded onto the plate. Also loaded was a buffer blank, a negative control of about 1 μg of protein sample from non-transgenic plant tissue and a 4 ng insulin positive control (created by loading 4 μl of a 1:1000 dilution of insulin, diluted in competition buffer). Plates were covered and incubated at 35° C. to 39° C., with a target temperature of 37° C. for 1.5 hours on a flat surface. The plates were washed four times with PBST. A streptavidin-alkaline phosphatase solution (from Jackson No. 016-050-084 or equivalent) was diluted 1:2,000 in competition buffer. 100 μl was added per well. The plates were covered and incubated at 35° C. to 39° C. for 50-70 minutes with a target time of 60 minutes. The plates were washed four times with PBST. A p-Nitrophenyl Phospate Disodium (pNpp) substrate (Sigma 104-105 or equivalent) tablet was diluted at 1 tablet per 5 ml of substrate buffer (pH 9.8). Once dissolved, 100 μl of substrate was added per well. The plates were covered and incubated at 35° C. to 39° C., with a target temperature of 37° C. for 25-35 minutes with a target time of 30 minutes. The plates were read at either 405 nm or 450 nm.

Figure 4:
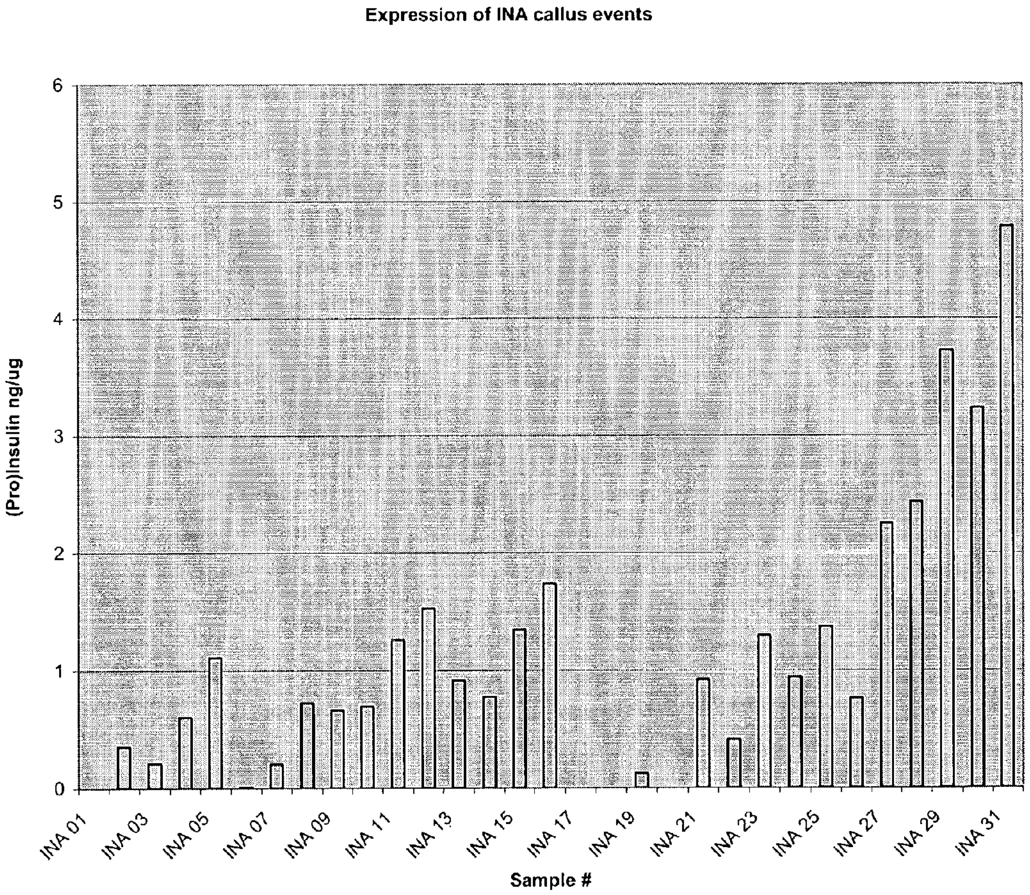
FIG. 4 is a graph showing the results of an assay for an insulin compound in plant tissue.

FIG. 4 shows the results of the assay of expression in callus tissue resulting from 31 independent transformation events. By measuring antibody reaction against insulin molecules, it can be seen that expression levels were achieved up to 4.8 ngμg$^{-1}$ of total soluble protein (0.48% total soluble protein).

Figure 5:
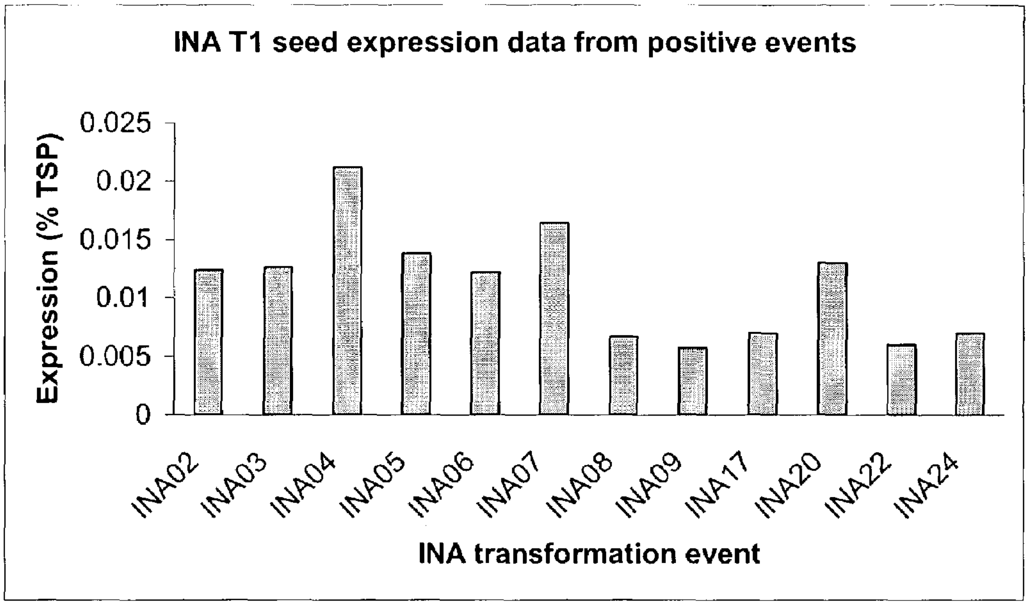
FIG. 5 is a graph showing the results of an assay for an insulin compound in maize seeds.

FIG. 5 shows the results of the assay of expression in seed tissue harvested from plants that were regenerated from 24 of the above 31 independent transformation events. In the case of seed, by measuring antibody reaction against insulin molecules, expression levels of up to 0.2 ngμg$^{-1}$ of total soluble protein (0.02% total soluble protein) were recorded.

EXAMPLE 3

Partial Purification from Seed

The presence of insulin or an insulin like compound in seed was verified by partially purifying the protein from a pool of expressing seed and demonstrating a signal with this material of over 40 fold above negative control levels using the above ELISA. Partial purification was achieved using anion exchange column chromatography. Approximately 30 g of seed was pooled from plants that had been pollinated using pollen from INA05 $T_0$ plants. The pooled seed was ground in a coffee grinder, and extracted with 105 ml of Buffer A (20 mM BisTris, pH 6.5) containing 50 mM NaCl by rotating the sample slowly at 4° C. for 30 minutes. The sample was centrifuged for 15 minutes at 2000×g to sediment insoluble debris, and the resulting supernatant (55 ml) was combined with an equal volume of buffer A. This diluted sample was filtered through a 0.2 □M membrane, and the resulting extract (100 ml) was subjected to chromatography on a 5 ml HiTrap Q column (Amersham Pharmacia Biotech) equilibrated in 2.5% Buffer B (Buffer A containing 1000 mM NaCl). The column was developed at 2 ml per minute with 4 column volumes of 2.5% buffer B followed first by a linear 40 ml gradient to 32.5% buffer B, and then a 4 ml gradient to 100% buffer B. Unbound (flow through) materials were collected in 5 ml fractions, and eluted proteins were collected in 2 ml fractions. Aliquots of each fraction were examined for protein content by the Bradford assay, cited above, and for insulin content by competition ELISA.

Figure 6:
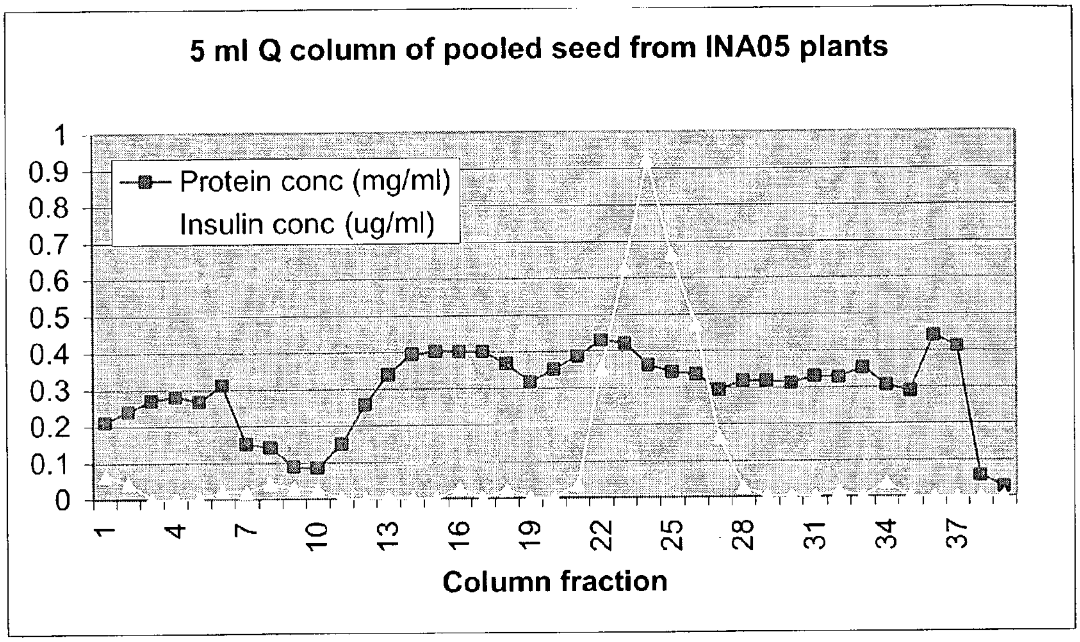
FIG. 6 is a graph showing the partial purification of an insulin compound from plant tissue.

The results of a representative one of two such experiments using a 5 ml HiTrap Q column are shown in FIG. 6. In addition there were five 1 ml column runs that gave similar results. For the 5 ml column data shown in FIG. 6, the level of the insulin compound in the starting pool of seed is approximately 0.007% of total soluble protein, and this is enriched 35 fold in the fraction with peak insulin activity, giving a level of approximately 0.26% of total soluble protein.

What is claimed is:

1. A monocotyledonous plant stably transformed with a a nucleotide sequence encoding a proinsulin or insulin protein, wherein expression of said protein is directed to seed of said plant, and wherein said protein is expressed at levels of at least 0.20% total soluble seed protein;

said protein not fused to cholera toxin B subunit.

2. The plant of claim 1, wherein the plant is maize.

3. A method of producing a proinsulin or insulin protein in a monocotyledonous plant comprising: introducing into the plant a construct comprising a nucleotide encoding a proinsulin or insulin protein operably linked to a maize globulin 1 promoter and a barley alpha amylase signal sequence, wherein the protein is expressed in seed of said plant at levels of at least 0.20% of total soluble seed protein; and extracting the protein from the seed.

4. The method of claim 3, wherein the plant is maize.

* * * * *

SEQUENCE LISTING

```
<160> NUMBER OF SEQ ID NOS: 2

<210> SEQ ID NO 1
<211> LENGTH: 258
<212> TYPE: DNA
<213> ORGANISM: Homo sapiens

<400> SEQUENCE: 1

ttcgtgaacc agcacctctg cggctcccac ctcgtggagg ccctctacct cgtgtgcggc      60

gagcgcggct tcttctacac cccgaagacc cgcagggagg ccgaggacct ccaggtgggc     120

caggtggagc tcggcggtgg cccgggcgcc ggctccctcc agccgctcgc cctcgagggc     180

tccctccaga agcgcggtat cgtggagcag tgctgcacct ctatctgctc cctctaccag     240

ctcgagaact actgcaac                                                   258


<210> SEQ ID NO 2
<211> LENGTH: 110
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 2

Met Ala Asn Lys His Leu Ser Leu Ser Leu Phe Leu Val Leu Leu Gly
  1               5                  10                  15

Leu Ser Ala Ser Leu Ala Ser Gly Phe Val Asn Gln His Leu Cys Gly
             20                  25                  30

Ser His Leu Val Glu Ala Leu Tyr Leu Val Cys Gly Glu Arg Gly Phe
         35                  40                  45

Phe Tyr Thr Pro Lys Thr Arg Arg Glu Ala Glu Asp Leu Gln Val Gly
     50                  55                  60

Gln Val Glu Leu Gly Gly Gly Pro Gly Ala Gly Ser Leu Gln Pro Leu
 65                  70                  75                  80

Ala Leu Glu Gly Ser Leu Gln Lys Arg Gly Ile Val Glu Gln Cys Cys
                 85                  90                  95

Thr Ser Ile Cys Ser Leu Tyr Gln Leu Glu Asn Tyr Cys Asn
            100                 105                 110
```